US00PP24508P2

(12) United States Plant Patent
Saul

(10) Patent No.: US PP24,508 P2
(45) Date of Patent: May 27, 2014

(54) ***KNIPHOFIA* PLANT NAMED 'ECHO DUO'**

(50) Latin Name: *Kniphofia uvaria*
Varietal Denomination: Echo Duo

(75) Inventor: Richard G. Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 171 days.

(21) Appl. No.: 13/507,434

(22) Filed: Jun. 26, 2012

(51) Int. Cl.
*A01H 5/00* (2006.01)

(52) U.S. Cl.
USPC ..... Plt./443

(58) Field of Classification Search
CPC ..... A01H 5/02
USPC ..... Plt./443
See application file for complete search history.

*Primary Examiner* — June Hwu
(74) *Attorney, Agent, or Firm* — Penny J. Aguirre

(57) ABSTRACT

A new cultivar of *Kniphofia*, 'Echo Duo', characterized by its bicolor inflorescences with flowers that emerge orange-red and mature to creamy white, its early blooming habit with repeat bloom throughout the summer, its semi-evergreen foliage that remains clean, its dense clump-forming habit with upright stems that do not lodge, its ability to readily produces side shoots with each shoot producing blooms and its ability to produce blooms on young plants.

2 Drawing Sheets

Botanical classification: *Kniphofia uvaria.*
Varietal denomination: 'Echo Duo'.

CROSS REFERENCE TO A RELATED APPLICATION

This application is related to a U.S. Plant Patent Application filed for a plant derived from the same breeding program that is entitled *Kniphofia* Plant Named 'Echo Mango' (U.S. Plant Pat. No. 21,706).

BACKGROUND OF THE INVENTION

The present invention relates to a new and distinct cultivar of *Kniphophia uvaria* and will be referred to hereafter by its cultivar name, 'Echo Duo'. 'Echo Duo' is a new cultivar of red hot poker or torch lily, a perennial grown for landscape use.

The new cultivar was derived from a controlled breeding program conducted by the Inventor at his nursery in Dahlonega, Ga. The overall purpose of the breeding program is to make selections of *Kniphofia* with unique flower colors combined with a reblooming habit. 'Echo Duo' was selected in the Inventor's trial bed in June 2007 as a single unique plant from amongst the seedlings derived from a cross made in April 2006 between 'Firelight' (not patented) as the female parent and 'Candle Light' (U.S. Plant Pat. No. 12,343) as the male parent.

Asexual reproduction of the new cultivar was first accomplished by division by the Inventor in Dahlonega, Ga. in June of 2007. The characteristics of this cultivar have been determined both by division and in vitro propagation to be stable and to reproduce true to type in successive generations.

SUMMARY OF THE INVENTION

The following traits have been repeatedly observed and represent the characteristics of the new cultivar of *Kniphofia*. These attributes in combination distinguish 'Echo Duo' from all other selections of *Kniphofia* known to the Inventor.

1. 'Echo Duo' exhibits an early blooming habit with the first blooms appearing at the end of April to the first part of May in Georgia.
2. 'Echo Duo' exhibits a re-blooming habit with repeat bloom throughout the summer.
3. 'Echo Duo' exhibits semi-evergreen foliage that remains cleaner than is typical of the species.
4. 'Echo Duo' exhibits a dense clump-forming habit with upright stems that do not lodge.
5. 'Echo Duo' readily produces side shoots with each shoot producing blooms.
6. 'Echo Duo' reaches a height of 100 cm (40 inches).
7. 'Echo Duo' produces blooms on young plants; a plug form tissue culture will produce blooms in about 4 weeks after roots are fully developed.
8. 'Echo Duo' exhibits bicolor inflorescences with flowers that emerge orange-red and mature to creamy white.

'Echo Duo' can be distinguished from its parent plants. The female parent, 'Firelight', differs from 'Echo Duo' in having flowers that are orange-red in color (do not turn creamy white) and in blooming only in spring. The male parent, 'Candle Light', differs from 'Echo Duo' in flowering stems that are shorter and tend to flop, in having flowers that are yellow in color, and in having leaves that are thinner in substance. 'Candle Light' is similar to 'Echo Duo' in having a re-blooming habit. 'Echo Duo' can be distinguished from typical plants of the species, *Kniphofia uvaria*, which differ from 'Echo Duo' in lacking a re-blooming habit, in having much taller flowering stems that tend to flop, and in having flowers that are orange-red and yellow. 'Echo Duo' can also be compared to the cultivars 'First Surprise' (U.S. Plant Pat. No. 16,036) and 'Echo Mango'. 'First Surprise' is similar to 'Echo Duo' in having an early blooming habit but differs from 'Echo Duo' in being shorter in height, in lacking a re-blooming habit, and in having inflorescences that are bright orange in color. 'Echo Mango' differs from 'Echo Duo' in having inflorescences that are apricot in color.

BRIEF DESCRIPTION OF THE DRAWING

The accompanying colored photographs illustrate the overall appearance and distinct characteristics of the new *Knipho-*

*fia*. The photographs were taken of six month-old plants as grown in two-quart containers in Alpharetta, Ga.

Figure 1:
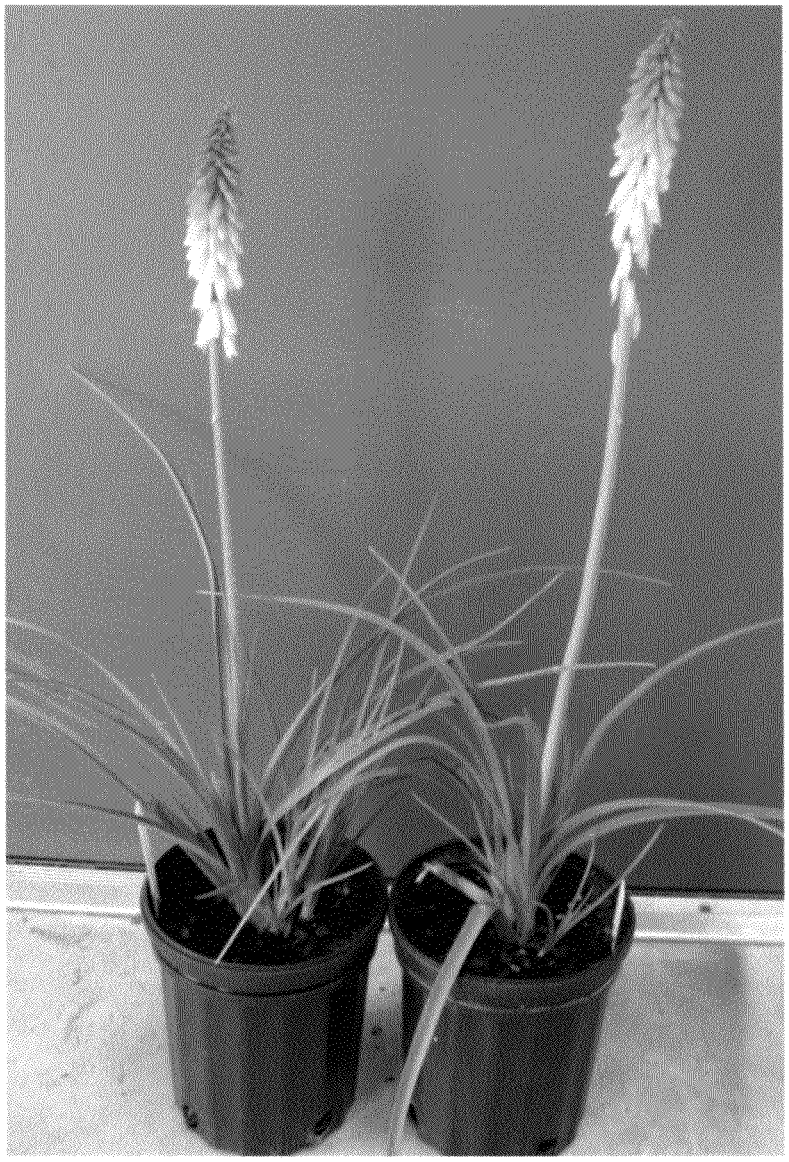

The photograph in FIG. 1 illustrates the overall habit and appearance of 'Echo Duo' in bloom and illustrates its upright flowering stems.

Figure 2:
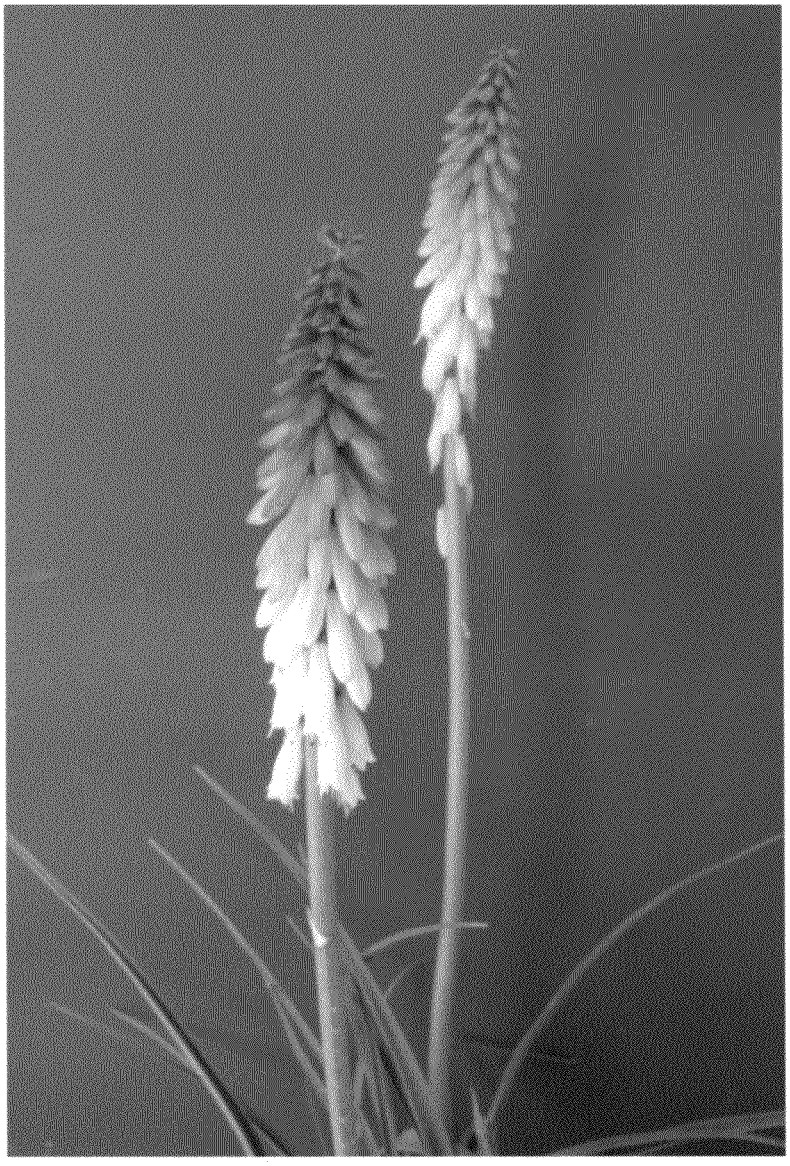

The photograph in FIG. 2 provides a close-up view of the inflorescences of 'Echo Duo'.

The colors in the photograph may differ slightly from the color values cited in the detailed botanical description, which accurately describe the colors of the new *Kniphofia*.

DETAILED BOTANICAL DESCRIPTION

The general observations describe plants of 'Echo Duo' that were observed for 2 years in a trail garden in Dahlonega, Ga., while the detailed botanical data describe six month-old plants as grown in two-quart containers in Alpharetta, Ga. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming habit.*—Commences bloom in late April to early may with repeat bloom throughout the summer.

*Plant type.*—Semi-evergreen perennial.

*Plant habit.*—Clump-forming basal grass-like leaves with upright flowers stems emerging from center of each division.

*Height and spread.*—About 100 cm (40 inches) in height in bloom and 61 cm (24 inches) in spread.

*Hardiness.*—U.S.D.A. Zones 6 to 9.

*Diseases and pests.*—No unique aspects concerning susceptibility or resistance to diseases or pests has been observed.

*Environmental stresses.*—Semi-evergreen foliage remains clean (cleaner than is typical of the species).

*Root description.*—Fleshy and thick.

Growth and propagation:

*Propagation.*—Tissue culture (preferred) or division.

*Time required for root development.*—A 2-inch plug from a tissue culture plantlet can be finished in about 6 weeks at 27° C. in summer (8 weeks in winter).

*Growth rate.*—Vigorous, readily produces side shoots; a mature plant 61 cm in spread has an average of 15 shoots.

Foliage description:

*Leaf shape.*—Linear.

*Leaf division.*—Simple.

*Leaf base.*—Truncate and sheathed to base of shoot.

*Leaf apex.*—Narrowly acuminate.

*Leaf aspect.*—Sulcate, leaves initially emerge upright, then upright to slightly cascading.

*Leaf venation.*—Parallel, the midrib is raised on the lower surface, not prominent or conspicuous, color matches leaf color.

*Leaf margins.*—Entire, scabrous.

*Leaf attachment and arrangement.*—Sessile, arise in rosette-like.

*Leaf size.*—Average of 1 cm in width (at midpoint) and up to about 40 cm in length when mature.

*Leaf number.*—Average of 14 per rootstock (shoot).

*Leaf surface.*—Puberulent on upper and lower surface.

*Leaf color.*—Newly emerging leaves upper and lower surfaces: 137B becoming 145A new base, mature leaves upper and lower surface; 137A becoming 145A near base.

Flower description:

*Inflorescence type.*—Dense racemes of single flowers held on erect and strong scapes.

*Inflorescence size.*—Reaches up to 14 cm in height and about 6 cm in width.

*Flower fragrance.*—None.

*Flower quantity.*—An average of 54 flowers per raceme, up to 15 racemes per clump in a season.

*Flower lastingness.*—Flowers open from base towards the apex, average of 5 days per flower, not persistent.

*Flower buds.*—Oblanceolate in shape, average of 2.5 cm in diameter and 7 mm in length, color; emerge 34A, changing to 34B, then 34C, then 34D in color and maturing to 4D and slightly suffused with 34D prior to opening.

*Flower aspect.*—Held horizontally then slightly downward at about a 45° angle as they mature.

*Flower shape.*—Narrowly campanulate-tubular.

*Flower size.*—About 3 cm in length and 5 mm in diameter.

*Tepals.*—6, fused with triangular-shaped free apex about 2.5 mm in width and 2 mm in length, margin is entire, apex is broadly acute, upper and lower surface is glabrous, satiny and waxy, color when opening inner and outer surface; 34D, color when fully open outer and inner surface; 157D and 145B at very base, fades to 1D.

*Peduncles* (*scapes*).—About 57 cm in length (from base of plant to top of raceme) and an average of 6 mm in width, held very erect, strong, color is a blend of 144A, 144B and 144C, surface is glabrous, slightly glaucous and satiny.

*Pedicels.*—Average of 2 mm in length and 1 mm in width, 144C in color, surface is glabrous and waxy.

Reproductive organs:

*Gynoecium.*—1 Pistil, stigma is crested, minute and 145B in color, style is about 2.3 cm in length, <1 mm in width, and 155D in color, ovary is superior, oblong in shape, about 4 mm in length and 2 mm in width and 144B in color.

*Androcoecium.*—6 stamens, anthers are oblong in shape, dorsifixed, about 2 mm in length and 1.5 mm width and 7B in color maturing to 164A in color, filaments are about 2.9 cm in length and 155D in color, pollen was moderate in quantity and 1D in color.

*Fruit and seed.*—Capsules; produced more abundantly when grown outdoors, ovoid-globose in shape, 3-parted, about 8 mm in length and width, a blend of 144A and 147A in color maturing to a blend of N200A, N200B, and 199A on the outer surface and 199B on the inner surface, glaucous surface becoming woody when mature, seeds; 3 per capsule, about 4 mm in length, 200A in color.

It is claimed:

1. A new and distinct cultivar of *Kniphofia* plant named 'Echo Duo' as herein illustrated and described.

* * * * *